(12) United States Patent
Kim et al.

(10) Patent No.: US 11,065,474 B2
(45) Date of Patent: Jul. 20, 2021

(54) PATIENT ALIGNMENT METHOD AND SYSTEM USING LIGHT FIELD AND LIGHT REFLECTOR DURING RADIATION THERAPY

(71) Applicant: THE CATHOLIC UNIVERSITY OF KOREA INDUSTRY-ACADEMIC COOPERATION FOUNDATION, Seoul (KR)

(72) Inventors: Tae-Ho Kim, Gyeonggi-do (KR); Seong-Hee Kang, Gyeonggi-do (KR); Dong-Su Kim, Gyeonggi-do (KR); Min-Seok Cho, Gyeonggi-do (KR); Dong-Seok Shin, Incheon (KR); Tae-suk Suh, Seoul (KR); Kyeong-Hyeon Kim, Gyeonggi-do (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 254 days.

(21) Appl. No.: 16/327,710

(22) PCT Filed: Aug. 30, 2016

(86) PCT No.: PCT/KR2016/009622
§ 371 (c)(1),
(2) Date: Feb. 22, 2019

(87) PCT Pub. No.: WO2018/038299
PCT Pub. Date: Mar. 1, 2018

(65) Prior Publication Data
US 2019/0209866 A1    Jul. 11, 2019

(30) Foreign Application Priority Data
Aug. 25, 2016 (KR) .......................... 10-2016-0108495

(51) Int. Cl.
*A61B 5/00* (2006.01)
*A61N 5/10* (2006.01)
*A61B 5/08* (2006.01)

(52) U.S. Cl.
CPC .......... *A61N 5/1049* (2013.01); *A61B 5/0077* (2013.01); *A61B 5/0816* (2013.01);
(Continued)

(58) Field of Classification Search
CPC .. A61N 5/1048; A61N 5/1049; A61N 5/1064; A61N 2005/1056; A61N 2005/1059; A61B 5/0077
See application file for complete search history.

(56) References Cited

U.S. PATENT DOCUMENTS

| 5,446,548 A * | 8/1995 | Gerig .......................... A61B 6/08 |
| | | 250/462.1 |
| 2012/0161767 A1 | 6/2012 | Hardy et al. |

(Continued)

FOREIGN PATENT DOCUMENTS

JP 2009-226015 A 10/2009
JP 2012-130700 A 7/2012
(Continued)

*Primary Examiner* — John P Lacyk
(74) *Attorney, Agent, or Firm* — Hoffmann & Baron, LLP

(57) ABSTRACT

A system to align an object using a light reflector, including: an input unit for pre-setting a first region in which radiation is to be emitted to the object; a display unit for displaying information on the first region; a radiation unit for emitting radiation to the first region; a reflector formed to correspond to the shape of the first region and configured to be attached to the first region; a light unit for emitting light in the same direction as the radiation to the first region; a camera for photographing a region of the reflector when the reflector reflects light emitted by the light unit; and a control unit for controlling the display unit to display the region of the light reflector which reflects light photographed by the camera, (Continued)

and determining whether the radiation is aligned to the first region of the object based on whether the region of the light reflector is included in the shape of the first region.

12 Claims, 7 Drawing Sheets

(52) U.S. Cl.
CPC ............ *A61B 5/721* (2013.01); *A61N 5/1067* (2013.01); *A61N 5/1068* (2013.01); *A61N 2005/1059* (2013.01); *A61N 2005/1074* (2013.01)

(56) References Cited

U.S. PATENT DOCUMENTS

| | | | |
|---|---|---|---|
| 2015/0202463 A1 | 7/2015 | Lim et al. | |
| 2019/0105514 A1* | 4/2019 | Amstutz | ................ A61B 90/39 |

FOREIGN PATENT DOCUMENTS

| | | |
|---|---|---|
| KR | 10-2001-0029530 A | 4/2001 |
| KR | 10-2001-0099718 A | 11/2001 |
| KR | 10-1470522 B1 | 12/2014 |

* cited by examiner

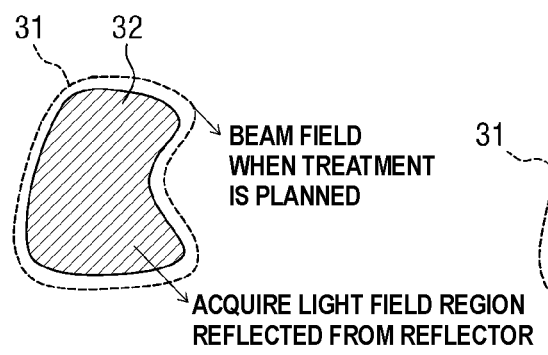
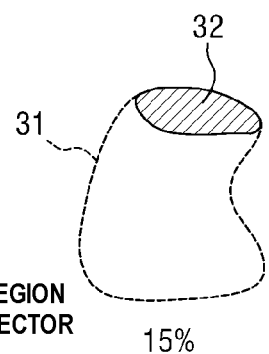
FIG. 5A
FIG. 5B
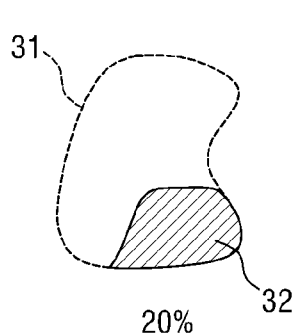
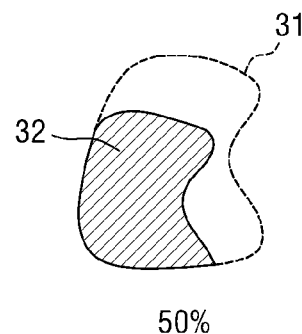
FIG. 5C
FIG. 5D
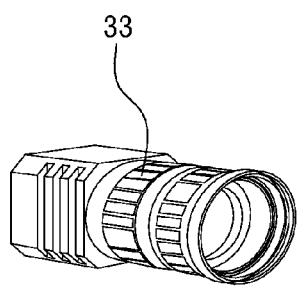
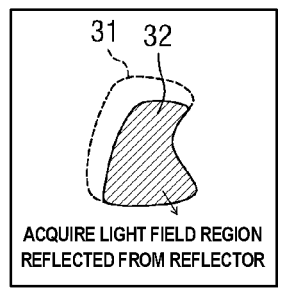
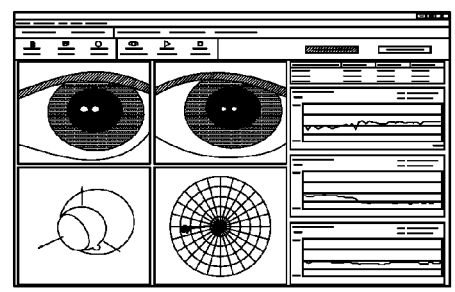
FIG. 6A
FIG. 6B
FIG. 6C

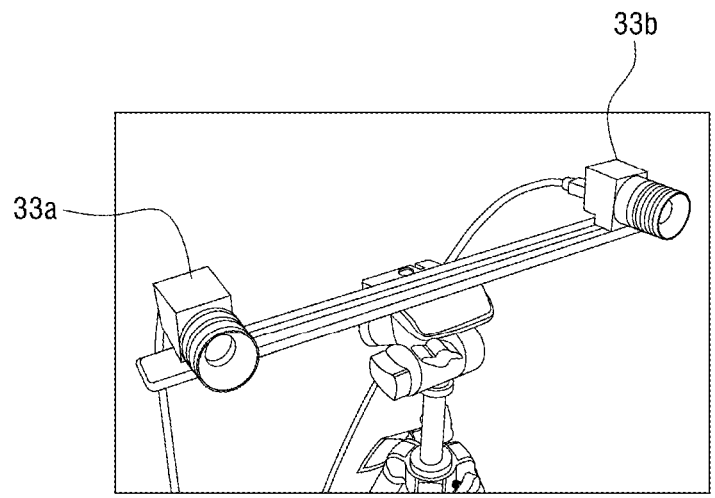
FIG. 7
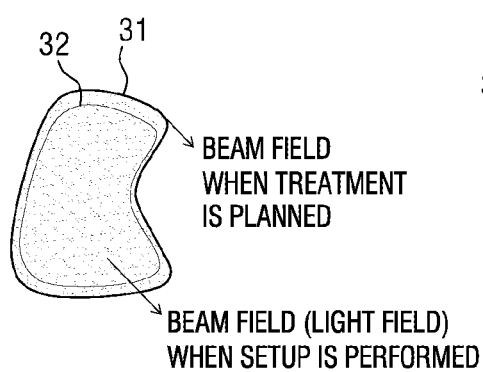 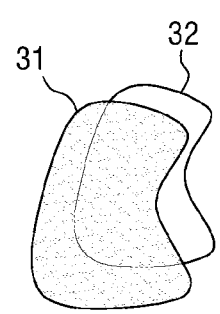
FIG. 8A — BEAM FIELD WHEN TREATMENT IS PLANNED; BEAM FIELD (LIGHT FIELD) WHEN SETUP IS PERFORMED
FIG. 8B
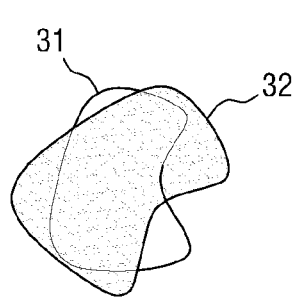 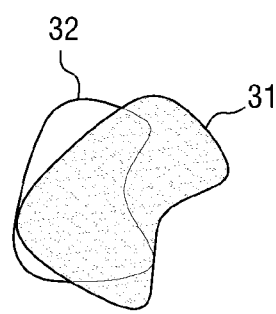
FIG. 8C
FIG. 8D

PATIENT ALIGNMENT METHOD AND SYSTEM USING LIGHT FIELD AND LIGHT REFLECTOR DURING RADIATION THERAPY

CROSS-REFERENCE TO RELATED APPLICATIONS

The present application in the U.S. National Phase of PCT/KR2016/009622, filed on Aug. 30, 2016, which claims priority to Korean Patent Application No. 10-2016-0108495, filed on Aug. 25, 2016, the entire contents of which are incorporated herein by reference.

BACKGROUND

Technical Field

The present invention relates to a beam field based patient alignment method and system using a light field and a body surface adhering light reflector. More specifically, the present invention relates to a method and a device in which a light field reflector, having the same size and the same shape as a beam field set at the time of establishing a treatment plan, is attached to a body surface of a patient and then a light field is emitted from a gantry head onto a region of the light field reflector attached to the body surface of the patient, a reflected light field is continuously acquired using a camera based imaging device, and quantitative analysis is performed to analyze whether a radiation therapy beam that is incapable of visual observation is accurately incident onto the body surface of the patient through real-time comparison of the reflected light field with the beam field set at the time of establishing a treatment plan.

Description of the Related Art

The radiation therapy is a method which damages or destroys a target tissue using high energy waves such as X-rays, gamma rays, or high energy particles such as electron beams or proton rays, to delay or stop the growth of malignant tissue or destroy the malignant tissue.

The radiation therapy is used to cure not only cancers, but also benign tumors, internal medical diseases, and some skin diseases.

Recently, instead of a neurosurgical operation which incises a skull, there has been developed a radiosurgery method which emits a large amount of radiation at one time to cure the disease without performing an incision surgery.

Further, the radiation therapy is generalized such that approximately 60% or more of cancer patients receive the radiation therapy.

The radiation therapy is not only used to cure the tumor, but also used together with other surgical operations that treat large and invasive tumors, which are hard to be operated or a local part which is not removed by the operation, in order to reduce a size of the tumor to make the surgery easier or destroy malignant cells remaining after the surgery.

An external radiation therapy device which emits radiation from the outside may be classified into a low-energy X-ray therapy device, a radioisotope therapy device, a linear accelerator, and a particle accelerator, depending on a method which generates high energy particles or radiation.

The low-energy X-ray therapy device was used to cure skin diseases or deep parts using an X-ray generator but is rarely used at present.

The radioisotope therapy device uses gamma rays generated from a radioisotope such as cobalt 60 (Co-60). The radioisotope therapy device uses gamma rays having a stronger energy than that of the low-energy X-ray therapy device, but the usage thereof is gradually reduced.

The linear accelerator which is used as a standard of the radiation therapy outputs X-rays and the electron beams, transmits various energies, has a high dose rate, and adjusts the beam formation.

The particle accelerator has a structure in which neutron or proton particles accelerated in a cyclotron accelerator are transported through a beam transport tube and discharged to a desired portion through a nozzle. Therefore, the particle accelerator has a Bragg's peak which is deeper than that of the linear accelerator so that the dose is minimized for normal tissue and the energy is concentrated only in deep tumors.

In the meantime, a computerized tomography (CT) which is the most famous as a diagnostic device using radiation, is a technique which emits X-rays onto a biological tissue while rotating around the biological tissue, detects an intensity of the X-rays which pass through the biological tissue at an opposite side, and reconstructs a tomographic image based on detected data.

Generally, in such a medical radiation device, the more the position of a patient is intentionally changed or a patient unconsciously moves, the lower the diagnostic accuracy or the treatment effect, and the higher a radiation dose absorbed onto a normal tissue around a lesion and the more time and cost are required.

Therefore, the medical radiation device has developed such that a radiation emitting head and a detecting unit are fixed to be opposite to each other, and then improved such that the radiation emitting head and the detecting unit move around the patient.

Recently, the medical radiation device is mainly being improved to have a configuration in which a radiation emitting head is mounted in a gantry having an L, U, and C type arm, or a configuration having a ring-shaped gantry.

In the meantime, accurate pretreatment setup prior to the radiation therapy and the maintaining of the accuracy of the intra-fraction patient setup during the radiation therapy are very important factors which determine the results of the radiation therapy.

In order to satisfy the above-mentioned requirements, various monitoring methods such as a patient alignment method using a laser system and a patient alignment method using a stereovision technology are proposed.

However, these monitoring methods are not very helpful to improve the accuracy due to technical limitations and lack of verification.

In order to transmit an accurate dose to the tumor, it is ideal to perform the setup based on the position of the tumor.

However, when real-time monitoring is performed using radiation such as X-ray or CT for the above-mentioned purpose, an imaging dose more than necessary may be transmitted to the patient, which may cause problems.

Currently, even though in clinical practices, a beam field-based patient setup is performed as an alternative, it is unreliable to ensure the accuracy because the patient setup is performed depending on the user's experience (visually confirmed by human) without performing quantitative verification.

That is, there are no quantitative evaluation method and no commercially available monitoring device for the beam field-based patient setup which is clinically used, but the beam field-based patient setup is performed only depending on the experience and knowhow of radiographers.

Further, only one checking process is provided before the radiation therapy, but appropriate preparations for changes during the treatment are not proposed.

Therefore, a system and method for solving the above-described problems are required.

SUMMARY OF THE INVENTION

An object of the present invention is to provide a patient alignment method and system using a light field and a body surface adhering light reflector.

More specifically, an object of the present invention is to provide a method and a device which attach a reflector having the same size and the same shape as a beam field set at the time of establishing a treatment plan to a body surface of a patient and then emit a light field from a gantry head onto a light field reflector attached to the body surface of the patient, continuously acquire the reflected light field using a camera based imaging device, and quantitatively compare and analyze whether a radiation therapy beam that is incapable of visual observation is precisely incident on the body surface of the patient through real-time comparison of the reflected light field with the beam field set at the time of establishing a treatment plan for the patient.

In the meantime, technical objects to be achieved in the present invention are not limited to the aforementioned technical objects, and another not-mentioned technical object will be obviously understood by those skilled in the art from the description below.

In order to achieve the above-described technical objects, according to an aspect of the present invention, a system to align an object using a light reflector includes: a user input unit which pre-sets a first region in which radiation is emitted to an object; a display unit which displays information on the first region; a radiation emitting unit which emits the radiation to the first region; a light reflector which is formed to correspond to a shape of the first region is configured to be attached to the first region of the object; a light emitting unit which emits light in the same direction as the radiation to the first region; a camera which photographs a region of the light reflector which reflects light when the light reflector reflects light emitted by the light emitting unit; and a control unit which controls the display unit to additionally display the region of the light reflector which reflects light photographed by the camera, and determines whether the radiation is aligned to the first region of the object based on whether the region of the light reflector is included in the shape of the first region.

Further, the control unit may double-check whether the radiation is emitted to the first region in a step of aligning the object to establish a plan for emitting radiation and a step of aligning the object to perform the treatment by emitting the radiation to the object.

Further, when the region of the light reflector deviates from the shape of the first region by at least a predetermined percentage, the control unit may stop the radiation emitting unit from emitting the radiation.

Further, the camera may be attached to the radiation emitting unit and the control unit may determine whether the radiation is emitted to the first region using a change in an area of region of the light reflector included in the shape of the first region.

Further, the system may include a plurality of cameras, and the control unit may determine changes in three-dimensional translation and rotation of the region of the light reflector with respect to the shape of the first region by a plurality of images acquired using the plurality of cameras, and the control unit may determine whether the radiation is emitted to the first region based on the changes.

Further, the system further includes a sensor which senses a respiratory signal related to breath of the object, and when the change in the respiratory signal deviates from a predetermined range, the control unit may stop the radiation emitting unit from emitting the radiation.

In order to achieve the above-described technical objects, according to another aspect of the present invention, a method of aligning an object using a light reflector includes: setting a first region in which radiation is to be emitted to the object; displaying information on the first region; attaching a light reflector to the first region of the object, the light reflector formed to correspond to a shape of the first region; emitting light in the same direction as a direction of the radiation to be emitted to the first region; displaying a region of the light reflector which reflects light using the light emitted, as photographed by a camera; establishing a radiation emitting plan for alignment of the object to the radiation to be emitted using whether the region of the light reflector is included in the shape of the first region.

Further, after establishing the radiation emitting plan for alignment of the object using whether the region of the light reflector is included in the shape of the first region, method may further include: emitting the radiation to the first region; emitting further light to the first region in the same direction as the radiation; displaying a further region of the light reflector which reflects light, as photographed by a camera; determining whether the radiation is aligned to the first region of the object based on whether the further region of the light reflector is included in the shape of the first region.

Further, after determining whether the radiation is aligned to the first region of the object based on whether the further region of the light reflector is included in the shape of the first region, method may further include: stopping emission of the radiation when the further region of the light reflector deviates from the shape of the first region by at least a predetermined percentage.

Further, in determining whether the radiation is aligned to the first region of the object based on whether the further region of the light reflector is included in the shape of the first region, it may be determined whether the radiation is aligned to the first region of the object based on at least one of a change in an area of the region of the light reflector included in the shape of the first region, and changes in three-dimensional translation and rotation of the region of the light reflector with respect to the shape of the first region.

Further, after determining whether the radiation is aligned to the first region of the object based on whether the further region of the light reflector is included in the shape of the first region, the method may further include: sensing a respiratory signal related to the breath of the object; and stopping emission of the radiation when a change in the respiratory signal deviates from a predetermined range.

According to the present invention, it is possible to provide a method and a system to align an object using a light field and a body surface adhering light reflector.

Specifically, according to the present invention, it is possible to attach a light field reflector having the same size and the same shape as a beam field set at the time of establishing a treatment plan to a body surface of a patient and then emit a light field from a gantry head onto the light field reflector attached to the body surface of the patient, continuously acquire the reflected light field using a camera based imaging device, and quantitatively compare and analyze whether a radiation therapy beam that is incapable of visual observation is precisely incident on the body surface of the patient through real-time comparison of the reflected light field with the beam field set at the time of establishing a treatment plan for the patient.

Further, according to the present invention, quantitative evaluation may be provided by a real-time analysis system and an error caused by human may be prevented.

Further, according to the present invention, in real time, it is possible to identify not only setup errors prior to the radiation therapy, but also errors generated during the therapy so that it may be very helpful to improve the radiation therapy results.

When the method and the system proposed by the present invention are used, quantitative analysis which was not possible by the human-dependent methods of the related art is possible and the monitoring is allowed even during the radiation therapy, so that it may be very helpful to improve the radiation therapy results.

Further, according to the present invention, in addition to the clinical advantages, a cost for the development is very small and in actual clinical application, there is no increase in an amount of work given to the user and no increase in the treatment time, so that it may be very advantageous for commercialization.

In the meantime, a technical object to be achieved in the present disclosure is not limited to the aforementioned effects, and another not-mentioned effect will be obviously understood by those skilled in the art from the description below.

BRIEF DESCRIPTION OF THE DRAWINGS

FIGS. 5A-5D illustrate specific examples where a reflection region of a body surface adhering light reflector deviates from a designed beam field region, based on a structure described in FIGS. 4A-4D.

FIGS. 6A-6C illustrate views for explaining a method of monitoring a change in an area of a reflection region using one camera, with respect to the present invention.

FIGS. 7 and 8A-8D are views for explaining a method of monitoring changes in three-dimensional translation and rotation of a patient body surface to which a light reflector is attached using two cameras, with respect to the present invention.

DETAILED DESCRIPTION OF THE EMBODIMENTS

Figure 1:
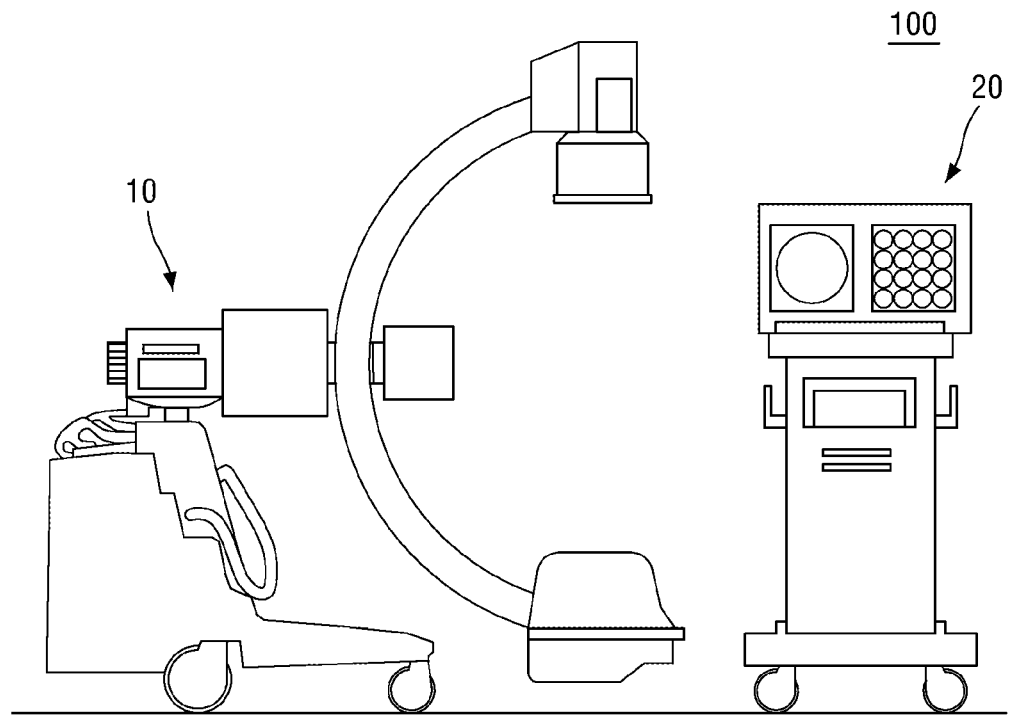
FIG. 1 illustrates a specific example of a patient alignment system including a medical radiation device which is generally used.
Figure 2:
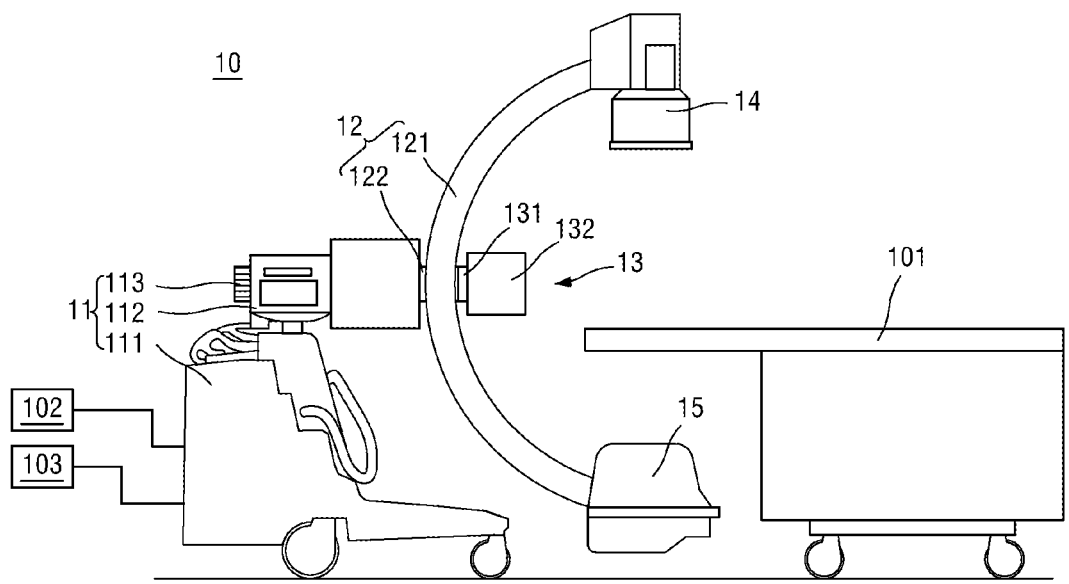
FIG. 2 illustrates a specific example of an image augmentation device among components of a medical radiation device which is generally used.

FIG. 1 illustrates a specific example of patient alignment system including a medical radiation device which is generally used, and FIG. 2 illustrates a specific example of an image augmentation device among components of a medical radiation device which is generally used.

Referring to FIG. 1, a patient alignment system 100 includes a medical radiation device according to the present invention configured by an image augmentation device 10 for acquiring images, and a display device 20 which displays the acquired images to a user or an operator.

Referring to FIG. 2, the image augmentation device 10 includes a body unit 11, a C-arm gantry 12, a therapeutic radiation unit 13, a diagnostic radiation emitting unit 14, and a diagnostic radiation detecting unit 15.

The image augmentation device 10 may further include a bed unit 101 on which a patient is located, a control unit 102, and a reading unit 103.

First, the body unit 11 provides a mechanical balance and support to the image augmentation device 10, and also provides a transport path of electromagnetic energy and high energy particles to the outside, which is required for individual units 13, 14, and 15. Specifically, the body unit 11 is erected from a floor on which the image augmentation device 10 is disposed at least to a plane in which an isocenter is located to support a weight of the C-arm gantry 12 of the image augmentation device 10. Further, in order to reduce risks of twisting, errors, and rollover due to the movement of the center of gravity during an operation, for example, various known support structures such as a counter-balancing structure may be adapted. The isocenter is a position in which radiations emitted from various positions are intensively transmitted so as to be selected to coincide with a specific portion of the body which requires the therapy or diagnosis. Therefore, a plane in which the isocenter is located may refer to a conceptual plane which is determined depending on a position of the lesion of the patient located or laying on the bed unit 101. The body unit 11 may have a base 111 which has wheels to move the image augmentation device 10 in a desired position or is movable on a predetermined track provided on the floor. Further, the body unit 11 may be mechanically fastened with a fixing unit 122 of the C-arm gantry 12 by a fixing unit 112 installed in a position which is in contact with a center of curvature of a circular arc of a C-arm 121 of the C-arm gantry 12. In this case, the fixing unit 122 of the C-arm gantry 12 may be fixed rotatably around the fixing unit 112 of the body unit 11. To this end, the body unit 11 may further include a rotary driving unit 113 such as a motor and a gear.

The C-arm gantry 12 may include the C-arm 121 and the fixing unit 122. The C-arm 121 has a curved C-shaped arc shape with one side opened and specifically, when the C-arm 121 is vertically erected and radiates heat, the C-arm is symmetrical with a plane where the isocenter is located and is open toward the isocenter. The fixing unit 122 of the C-arm gantry 12 mechanically couples at least a part of an outer surface of the C-arm 121 to the fixing unit 112 of the body unit 11. Desirably, the fixing unit 122 of the C-arm gantry 12 may be coupled to the fixing unit 112 of the body unit 11 on the outer surface of the center position of the curvature of the arc of the C-arm 121. Moreover, the fixing unit 122 of the C-arm gantry 12 may be pivotably and rotatably fastened with the fixing unit 112 of the body unit 11. In this case, the fixing unit 122 of the C-arm gantry 12 may be rotatably fastened with the body unit 11 with respect to an axis connecting a portion which is fixed to the body unit 11 and the isocenter.

The therapeutic radiation unit 13 may support a therapeutic radiation emitting head 132 which emits therapeutic radiation from a head support 131. In this case, the therapeutic radiation unit 13 may determine a position of the therapeutic radiation emitting head 131 in a specific position and at a specific angle on an inner surface of the C-arm 121 such that a dose of the therapeutic radiation emitted from the therapeutic radiation emitting head 132 is effectively applied to a target tissue at the isocenter, as indicated by the control unit 102 according to a predetermined dose plan.

According to an example embodiment, the therapeutic radiation emitting head 132 may emit X-rays, gamma rays, high-energy electrons, high-energy protons, or other high energy fine particles.

According to an example embodiment, the therapeutic radiation emitting head 132 may include any one of an X-ray generating device, a radioisotope source, and a linear accelerator. According to another example embodiment, the therapeutic radiation emitting head 132 receives high energy fine particle beam generated by being accelerated in the particle accelerator installed outside the image augmentation device 10 to emit the high energy fine particle beam. Further, according to an example embodiment, the therapeutic radiation emitting head 132 may be implemented by a multi-leaf collimator (MLC). When the multi-leaf collimator is used, the therapeutic radiation emitting head 132 may internally form the beam so that the radiation energy may be more efficiently transmitted.

The image augmentation device 10 may further include a therapeutic radiation source unit 14 and a therapeutic radiation detecting unit 15, which are mounted on the inner surface of the C-arm 121 to be opposite to each other with the isocenter therebetween. According to an example embodiment, the therapeutic radiation source unit 14 may include an X-ray source and the therapeutic radiation detecting unit 15 may include an X-ray detecting sensor. The therapeutic radiation source unit 14, the therapeutic radiation detecting unit 15, and the reading unit 103 may configure a computed tomographic imaging device (CT).

Even though not illustrated, the therapeutic radiation source unit 14 may include at least one camera.

Here, the camera may be used to monitor the change in an area of the reflection region to compare the reflection region of the body surface adhering light reflector and the designed beam field region.

Further, a plurality of cameras may be used to monitor the changes in the three-dimensional translation and rotation of the patient's body surface to which the light reflector is attached.

The bed unit 101 is configured so that the patient may lay thereon, and may include wheels or a track on a portion which is in contact with the floor according to an example embodiment.

The control unit 102 may control the driving of the fixing unit 112 and the rotating unit 113 of the body unit 11, and a therapeutic radiation emitting direction and intensity of the therapeutic radiation source unit 14 in accordance with a diagnosis plan input in advance and control the driving of the fixing unit 112 and the rotating unit 113 of the body unit 11, and a position, an angle, a direction, and beam formation of the therapeutic radiation unit 13 in accordance with a dose plan input in advance.

The reading unit 103 may analyze a signal detected by the therapeutic radiation detecting unit 15 to reconstruct the signal as a CT image.

In the meantime, the maintaining of accurate pretreatment setup prior to the radiation therapy and the accuracy of the intra-fraction patient setup during the radiation therapy are very important factors which determine the results of the radiation therapy.

In order to satisfy the above-mentioned requirements, various monitoring methods such as a patient alignment method using a laser system and a patient alignment method using a stereovision technology are proposed.

However, the methods are not very helpful to improve the accuracy due to technical limitations and lack of verification.

In order to transmit an accurate dose to the tumor, it is ideal to perform the setup based on the position of the tumor.

However, when real-time monitoring is performed using radiations such as X-ray or CT for the above-mentioned purpose, an imaging dose more than necessary may be transmitted to the patient, which may cause problems.

Currently, even though in clinical practices, a beam field-based patient setup is performed as an alternative, it is unreliable to ensure the accuracy because the patient setup is performed depending on the user's experience (visually confirmed by human) without performing quantitative verification.

That is, there are no quantitative evaluation method and no commercially available monitoring device for the beam field based patient setup which is clinically used, but the beam field based patient setup is performed only depending on the experience and knowhow of radiographers.

Further, only one checking process is provided before the radiation therapy, but appropriate preparations for changes during the treatment are not proposed.

Therefore, in order to solve the above-mentioned problems, the present disclosure is to provide a beam-field based patient setup method and system using a light field and a body surface adhering light reflector.

Specifically, according to the present invention, it is possible to provide a method and a device in which a light field reflector, having the same size and the same shape as a beam field set at the time of establishing a treatment plan, is attached to a body surface of a patient and then a light field is emitted from a gantry head onto a region of the light field reflector attached to the body surface of the patient, a reflected light field is acquired using a camera based imaging device, and quantitative analysis is performed to analyze whether a radiation therapy beam that is incapable of visual observation is precisely incident on the body surface of the patient through real-time comparison of the reflected light field with the beam field as set at the time of establishing a treatment plan.

Prior to specific description of the present invention, a light reflector which is applied to the present invention will be described.

The light reflector may include an object which emits (reflects) light based on light incident on the light reflector.

Here, light which is provided to the light reflector may be separately provided in the radiation emitting head 14 or may be provided in at least one camera 33.

Specifically, in the present invention, a light reflector which is attached to a body surface of a patient to be treated may be desirably used.

FIGS. 3A-3E illustrate a specific example of a body surface adhering light reflector which is applicable to the present invention.

Figure 3A:
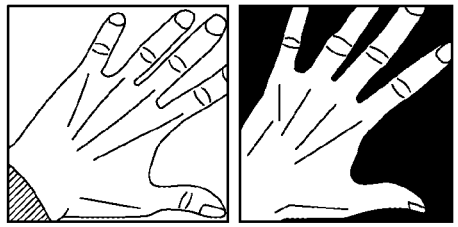
FIGS. 3A-3E illustrate specific examples of a body surface adhering light reflector applicable to the present invention.

Referring to FIG. 3A, after applying the light reflector on a hand, a state before emitting light and a state after emitting light are compared.

Figure 3B:

Referring to FIG. 3B, it is specifically illustrated that star-shaped light reflectors are closely attached to a body of a deer and then light is irradiated so that reflectors emit (reflect) light.

Figure 3C:
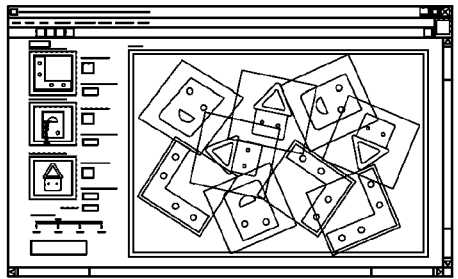

Referring to FIG. 3C, it is specifically illustrated that light reflectors are attached to a plurality of tools and light is projected so that the reflectors emit (reflect) light.

Figure 3D:
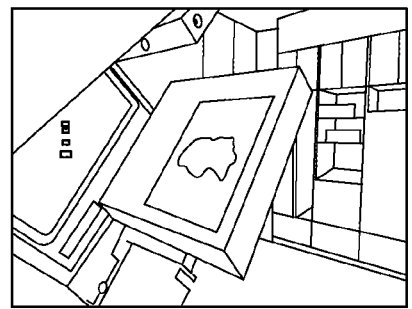

Referring to FIG. 3D, it is illustrated that a light reflector is attached to a specific region of radiation equipment and light is irradiated so that the light reflector emits (reflects) light from a specific region.

Figure 3E:
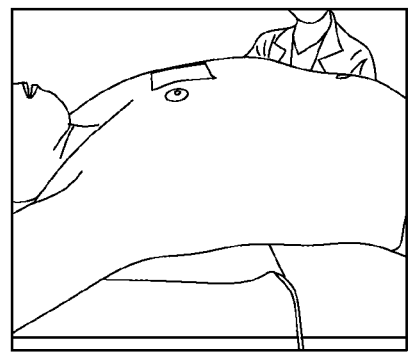

Referring to FIG. 3E, it is specifically illustrated that after closely attaching or applying the light reflector to a part of the patient's body, the light is irradiated so that the light reflector emits (reflects) light from a specific body region of the patient.

In the present invention, a method which identifies an emission region of invisible radiation in real time through use of a light reflector is described with reference to FIGS. 3A-3E.

That is, a region to which radiation is emitted is set in advance and a light reflector having a shape corresponding to the set region is attached to the patient's body.

Thereafter, light is projected in the same direction as radiation emitted by the emitting head (gantry head) 14 onto the set region and thus the light reflector emits (reflects) light.

Whether the region to which radiation is emitted and a region of the light reflector which emits (reflects) light coincide with each other may be identified by the display device 20 in real time.

When the regions do not slightly coincide with each other, it is possible make an adjustment such that the region of the light reflector to which light is projected coincides with the region to which the radiation is emitted by changing a fixed position of the patient.

Further, when the region to which the radiation is emitted and a region of the light reflector which emits (reflects) light are significantly different, the radiation therapy may be stopped.

The determination of whether the region to which radiation is emitted and the region of the light reflector which emits (reflects) light coincide with each other may also be double-checked before the radiation therapy and during the radiation therapy.

Accurate pretreatment setup prior to the radiation therapy and the maintaining of the accuracy of the intra-fraction patient setup during the radiation therapy are very important factors which determine the results of the radiation therapy. There is an advantage in that the setup of the patient in a planning step and a treatment step may be accurately performed according to the method proposed by the present invention.

FIGS. 4A-4D illustrate a specific example of comparing a reflection region of a body surface adhering a light reflector and a designed beam field region, with respect to the present invention.

Figure 4A:
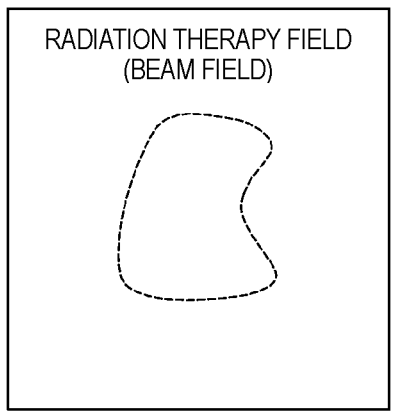
FIGS. 4A-4D illustrate specific examples of comparing a reflection region of a body surface adhering light reflector and a designed beam field region, with respect to the present invention.

FIG. 4A illustrates a specific example of a region to which a predetermined radiation is emitted, referred to as a beam field.

Figure 4B:
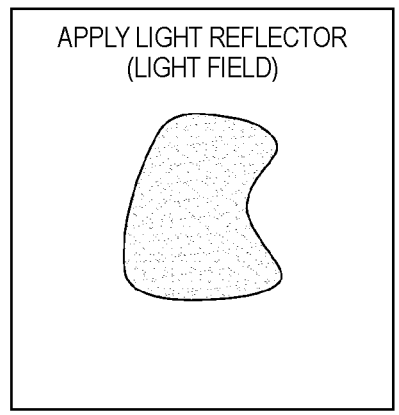

Further, FIG. 4B illustrates that a light reflector having a shape corresponding to the region of FIG. 4A to which the radiation is emitted is applied on a partial region of the body.

Figure 4C:
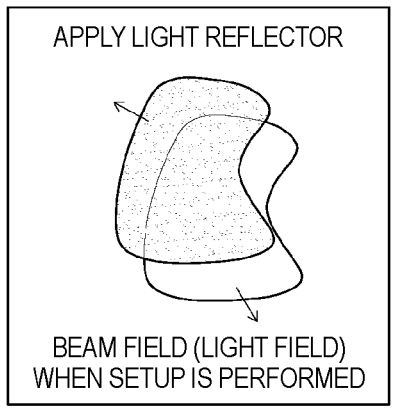

Further, FIG. 4C illustrates that a region of the light reflector which emits (reflects) light using the emitted light (light field) and a region to which the radiation is emitted (beam field) do not coincide with each other.

Figure 4D:
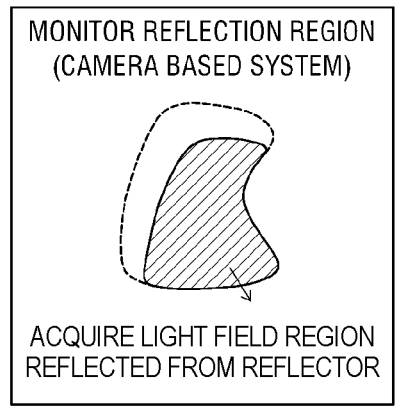

Further, FIG. 4D specifically illustrates that a region of the light reflector which emits (reflects) light using the emitted light and a region to which the radiation is emitted are adjusted using a camera.

Specifically, FIGS. 5A-5D illustrate a specific example that a reflection region of a body surface adhering light reflector deviates from a designed beam field region, based on a structure described in FIGS. 4A-4D.

Hereinafter, for the convenience of description, the region to which the radiation is emitted is referred to as a radiation therapy region 31 and the region of the light reflector which emits (reflects) light using the emitted light is referred to as a light reflector region 32.

Referring to FIG. 5A, the radiation therapy region 31 (beam field region) set in advance and the light reflector region 32 (light field region) having a corresponding shape are illustrated.

The light reflector region 32 may be formed to have completely the same area as the radiation therapy region 31 or to be smaller than the radiation therapy region 31.

FIG. 5B illustrates that the light reflector region 32 occupies only 15% of the radiation therapy region 31 due to movement of the patient and a change in surrounding conditions. In this case, it is desirable that the radiation therapy is stopped.

Further, FIG. 5C illustrates that the light reflector region 32 occupies only 20% of the radiation therapy region 31 due to movement of the patient and a change in surrounding conditions. In this case, it is also desirable that the radiation therapy is stopped.

Further, FIG. 5D illustrates that the light reflector region 32 occupies only 50% of the radiation therapy region 31 due to movement of the patient and a change in surrounding conditions. In this case, it is also desirable that the radiation therapy is stopped.

However, when the light reflector region 32 coincides with 80% or more of the radiation therapy region 31, it is possible to adjust the light reflector region 32 to be included in the radiation therapy region 31 by adjusting the patient or the equipment.

How much the light reflector region 32 is included in the radiation therapy region 31 may be determined by the following Equation 1.

$$\text{Beam field based setup accuracy} = \frac{\text{Reflection region beam field}}{\text{Beam field at time of establishing treatment plan}} \times 100 \quad \text{[Equation 1]}$$

Further, a specific method of determining whether the light reflector region 32 is included in the radiation therapy region 31 according to the present invention will be described with reference to the above description.

FIGS. 6A-6C illustrate is a view for explaining a method of monitoring a change in an area of a reflection region using one camera, with respect to the present invention.

Referring to FIG. 6A, one camera 33 according to the present invention may be used.

The camera 33 of FIG. 6A may be formed to be attached to the radiation emitting unit (gantry head) 14 so that an image for the light reflector region 32 may be acquired.

Further, using the camera 33 attached to the radiation emitting unit (gantry head) 14 as illustrated in FIG. 6B, it is determined whether the light reflector region 32 (light field region) is included in the radiation therapy region 31 (beam field region) by the method of monitoring a change in the area of an eye view of the light reflector region.

FIG. 6C illustrates a representative example of a driving state of a beam's eye view based video monitoring software.

Further, a plurality of cameras may be used to monitor changes in the three-dimensional translation and rotation of the patient's body surface to which the light reflector is attached.

FIGS. 7 and 8A-8D are views for explaining a method for monitoring changes in three-dimensional translation and rotation of a patient body surface to which a light reflector is attached using two cameras, with respect to the present invention.

Referring to FIG. 7, two cameras 33a and 33b which are applicable to the present invention are illustrated.

The two cameras 33a and 33b do not need to be attached to the radiation emitting unit (gantry head) 14, which is different from the one camera 33 of FIG. 6A, and may be disposed to be spaced apart from each other with a predetermined interval to detect the changes in the three-dimensional translation and rotation based on a specific reference.

Referring to FIG. 8A, a specific shape of a reference for determining whether the light reflector region 32 (light field region) is included in the radiation therapy region 31 (beam field region) is illustrated.

FIG. 8B illustrates a specific state that senses the change in the three-dimensional translation of the patient's body surface to which the light reflector is attached, using the two cameras 33a and 33b described with reference to FIG. 7.

FIG. 8C illustrates a specific state that senses the change in the rotation of the patient's body surface to which the light reflector is attached, using the two cameras 33a and 33b described with reference to FIG. 7.

FIG. 8D illustrates a specific state that simultaneously monitors the changes in the three-dimensional translation and the rotation of the patient's body surface to which the light reflector is attached, using the two cameras 33a and 33b described with reference to FIG. 7.

Further, according to the example embodiment of the present invention, a respirational therapy may also be performed by monitoring the light reflection region.

Figure 9:
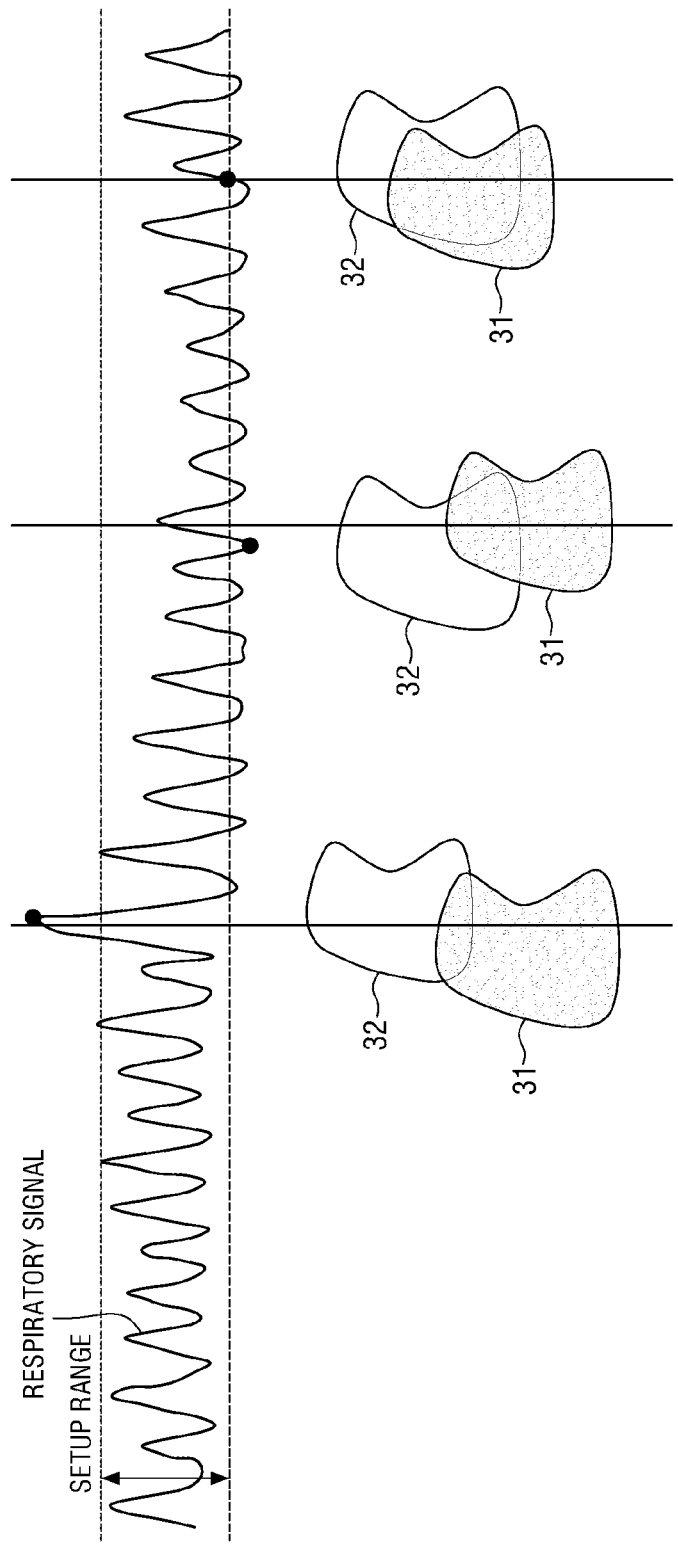
FIG. 9 is a view for explaining a respirational therapy by monitoring a light reflection region, with respect to the present invention.

FIG. 9 is a view for explaining a respirational therapy by monitoring a light reflection region, with respect to the present invention.

Referring to FIG. 9, it is confirmed that a respiratory signal deviates from a predetermined setup range so that an error of the beam field region is incurred.

Referring to (a), (b), and (c) regions of FIG. 9 indicated by vertical lines, it is confirmed that when the respiratory signal deviates from the setup range by the user, the light reflector region 32 deviates from the radiation therapy region 31.

Therefore, when the breath of the patient is monitored and a respiratory signal deviates from the specific setup range, a method of concluding that the light reflector region 32 leaves the radiation therapy region 31 and stopping the radiation therapy may be additionally used.

In the meantime, a method for maintaining the accurate patient setup prior to the radiation therapy and the accuracy of the patient setup during the radiation therapy will be described in detail based on the above-mentioned method for determining whether the light reflector region 32 deviates from the radiation therapy region 31.

Figure 10:
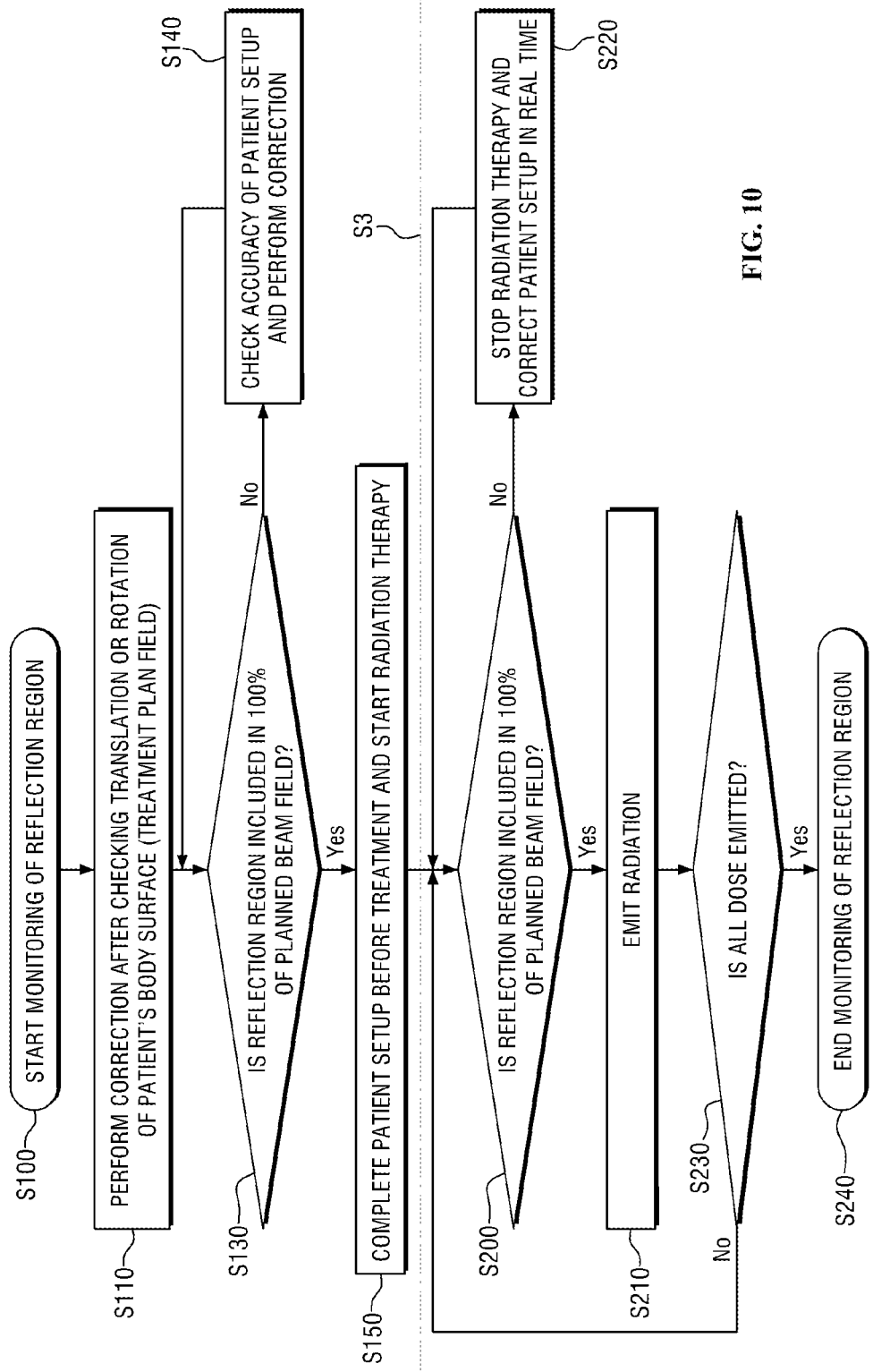
FIG. 10 is a flowchart of a method for maintaining an accurate patient setup prior to a radiation therapy and an accuracy of a patient setup during the radiation therapy, with respect to the present invention.

FIG. 10 is a flowchart of a method for maintaining an accurate patient setup prior to a radiation therapy and an accuracy of a patient setup during radiation therapy, with respect to the present invention.

Referring to FIG. 10, steps of aligning a patient prior to the treatment are illustrated above the line S3 and steps of monitoring patient setup during the therapy are illustrated below the line S3.

In both the steps of aligning a patient prior to the treatment and the steps of monitoring patient setup during the therapy, the method for determining whether the light reflector region 32 deviates from the radiation therapy region 31 may be applied.

Referring to FIG. 10, first, a step of starting the monitoring of the reflection region is performed in step S100.

Next, after checking translation or rotation of a patient's body surface, a correction related to the treatment plan field is performed in step S100.

That is, it is confirmed whether the light reflector region 32 is mapped to the radiation therapy region 31 by the method described with reference to FIGS. 8A-8D, in step S100, and if not, then correction is performed.

Moreover, a step of further checking whether the reflection region (light field region) is included in 100% of the planned radiation region (beam field region) is performed in step S130.

When the reflection region (light field region) is included in 100% of the planned radiation region (beam field region) in step S130, the patient setup before treatment is completed and the radiation therapy starts in step S150.

Otherwise, a step of checking the accuracy of the patient setup and modifying the patient setup is performed in step S140 and step S130 is performed again.

When the steps of aligning a patient prior to the treatment above the line S3 are completed, the steps of monitoring the patient setup during the treatment below the line S3 may be performed.

In the steps of monitoring patient setup during the treatment, first, it is determined whether the reflection region (light field region) is included in 100% of the planned radiation region (beam field region) in step S200.

When the reflection region (light field region) is included in 100% of the planned radiation region (beam field region) in step S200, the radiation is emitted in step S210, otherwise, a step of stopping the radiation therapy and modifying the patient setup in real time is performed in step S220.

After step S210, a step S230 of determining whether all therapeutic dose is emitted is performed in step S230 and when all therapeutic dose is emitted, the reflection region monitoring is completed in step S240, otherwise, the step S200 is performed again.

Therefore, when the alignment method and system using a light field and a body surface adhering light reflector according to the present invention as above mentioned are applied, it is possible to attach a light reflector having the same size and the same shape as a beam field set at the time of establishing a treatment plan to a body surface of a patient and then emit a light field from a gantry head onto a light field reflector attached to the body surface of the patient, continuously acquire the reflected light field using a camera based imaging device, and quantitatively compare and analyze whether a radiation therapy beam that is incapable of visual observation is precisely incident on the body surface of the patient through real-time comparison of the reflected light field with the beam field set at the time of establishing a treatment plan for the patient.

Further, according to the present invention, quantitative evaluation may be provided by a real-time analysis system and an error caused by a human may be prevented.

Further, according to the present invention, it is possible to identify not only setup errors prior to the radiation therapy, but also errors generated during the therapy in real time, so that it is very helpful to improve the results of the radiation therapy.

When the method and the monitoring system proposed by the present invention are used, quantitative analysis which was not possible by the human-dependent methods of the related art is possible and the monitoring is allowed even during the radiation therapy, so that it may be very helpful to improve the results of the radiation therapy.

Further, according to the present invention, in addition to the clinical advantages, a cost for the development is very small and in actual clinical application, there is no increase in an amount of work given to the user and increase in the treatment time, so that it may be very advantageous for commercialization.

As described above, the detailed description of the example embodiments of the disclosed present invention is provided such that those skilled in the art implement and carry out the present invention.

While the invention has been described with reference to the preferred embodiments, it will be understood by those skilled in the art that various changes and modifications of the present invention may be made without departing from the spirit and scope of the invention. For example, those skilled in the art may use configurations disclosed in the above-described example embodiments by combining them with each other. Therefore, the present invention is not intended to be limited to the above-described example embodiments but to assign the widest scope consistent with disclosed principles and novel features.

The present invention may be implemented in another specific form within the scope without departing from the essential feature of the present invention. Therefore, the detailed description should not be analyzed in a limited fashion but should be considered as providing examples of the present invention. The scope of the present invention should be determined by rational interpretation of the appended claims and all changes are included in the scope of the present invention within the equivalent scope of the present invention. The present invention is not intended to be limited to the above-described example embodiments but to assign the widest scope consistent with disclosed principles and novel features. Further, claims having no clear quoting relation in the claims are combined to configure the embodiment or may be included as new claims by correction after application.

What is claimed is:

1. A system to align an object using a light reflector, the system comprising:
    a user input unit which pre-sets a first region in which radiation is to be emitted to the object;
    a display unit which displays information on the first region;
    a radiation emitting unit which emits the radiation to the first region;
    a light reflector which is formed to correspond to a shape of the first region is configured to be attached to the first region of the object;
    a light emitting unit which emits light in the same direction as the radiation to the first region;
    a camera which photographs a region of the light reflector which reflects light when the light reflector reflects light emitted by the light emitting unit; and
    a control unit which controls the display unit to display the region of the light reflector which reflects light photographed by the camera, and determines whether the radiation is aligned to the first region of the object based on whether the region of the light reflector is included in the shape of the first region.

2. The system of claim 1, wherein the control unit double-checks whether the radiation is emitted to the first region in a step of aligning the object to establish a plan for emitting the radiation and a step of aligning the object to perform treatment by emitting the radiation to the object.

3. The system of claim 1, wherein when the region of the light reflector deviates from the shape of the first region by at least a predetermined percentage, the control unit stops the radiation emitting unit from emitting the radiation.

4. The system of claim 1, wherein the camera is attached to the radiation emitting unit and the control unit determines whether the radiation is emitted to the first region using a change in an area of the region of the light reflector included in the shape of the first region.

5. The system of claim 1, wherein the system comprises a plurality of cameras, the control unit determines changes in three-dimensional translation and rotation of the region of the light reflector with respect to the shape of the first region by a plurality images acquired using the plurality of cameras, and the control unit determines whether the radiation is emitted to the first region based on the changes.

6. The system of claim 1, further comprising a sensor which senses a respiratory signal related to breath of the object, wherein when a change in the respiratory signal deviates from a predetermined range, the control unit stops radiation emitting unit from emitting the radiation.

7. The system of claim 1, wherein the radiation and the light are simultaneously emitted.

8. A method of aligning an object using a light reflector, the method comprising:
    setting a first region which radiation is to be emitted to the object;
    displaying information on the first region;
    attaching a light reflector to the first region of the object, the light reflector formed to correspond to a shape of the first region;
    emitting light in the same direction as a direction of the radiation to be emitted to the first region;
    displaying a region of the light reflector which reflects light using the light emitted, as photographed by a camera; and
    establishing a radiation emitting plan for alignment of the object to the radiation to be emitted using whether the region of the light reflector is included in the shape of the first region.

9. The method of claim 8, wherein after establishing the radiation emitting plan for alignment of the object to the radiation to be emitted using whether the region of the light reflector is included in the shape of the first region, the method further comprising:
    emitting the radiation to the first region;
    emitting further light to the first region in the same direction as the radiation;
    displaying a further region of the light reflector which reflects light using the further light emitted, as photographed by the camera; and determining whether the radiation is aligned to the first region of the object based on whether the further region of the light reflector is included in the shape of the first region.

10. The method of claim 9, wherein after determining whether the radiation is aligned to the first region of the object based on whether the further region of the light reflector is included in the shape of the first region, the method further comprising stopping emission of the radiation when the further region of the light reflector deviates from the shape of the first region by at least predetermined percentage.

11. The method of claim 9, wherein in determining whether the radiation is aligned to the first region of the object based on whether the further region of the light reflector is included in the shape of the first region, it is determined whether the radiation is aligned to the first region of the object based on at least one of a change in an area of the region of the light reflector included in the shape of the first region, and changes in three-dimensional translation and rotation of the region of the light reflector with respect to the shape of the first region.

12. The method of claim 9, wherein after determining whether the radiation is aligned to the first region of the object based on whether the further region of the light reflector is included in the shape of the first region, the method further comprising:
  sensing a respiratory signal related to the breath of the object; and
  stopping emission of the radiation when a change in the respiratory signal deviates from a predetermined range.

* * * * *